(12) United States Patent
Baumgartner et al.

(10) Patent No.: US 11,628,015 B1
(45) Date of Patent: Apr. 18, 2023

(54) SYSTEMS AND METHODS FOR PERFORMING A SURGICAL PROCEDURE

(71) Applicants: James Edmund Baumgartner, Winter Park, FL (US); Kevin Ruda, Chanhassen, MN (US); Benjamin Osa, Chanhassen, MN (US)

(72) Inventors: James Edmund Baumgartner, Winter Park, FL (US); Kevin Ruda, Chanhassen, MN (US); Benjamin Osa, Chanhassen, MN (US)

( * ) Notice: Subject to any disclaimer, the term of this patent is extended or adjusted under 35 U.S.C. 154(b) by 777 days.

(21) Appl. No.: 16/534,679

(22) Filed: Aug. 7, 2019

Related U.S. Application Data

(60) Provisional application No. 62/715,912, filed on Aug. 8, 2018.

(51) Int. Cl.
| | | |
|---|---|---|
| *A61B 34/20* | (2016.01) | |
| *A61B 34/10* | (2016.01) | |
| *A61B 90/00* | (2016.01) | |
| *A61B 90/11* | (2016.01) | |

(52) U.S. Cl.
CPC .............. *A61B 34/20* (2016.02); *A61B 34/10* (2016.02); *A61B 90/11* (2016.02); *A61B 90/39* (2016.02); *A61B 2034/107* (2016.02); *A61B 2034/2068* (2016.02); *A61B 2090/363* (2016.02); *A61B 2090/374* (2016.02); *A61B 2090/3954* (2016.02); *A61B 2090/3983* (2016.02)

(58) Field of Classification Search
CPC .... A61B 2034/2055; A61B 2034/2068; A61B 2034/207; A61B 2034/2072; A61B 2090/0801; A61B 2090/363; A61B 2090/3916; A61B 2090/3937; A61B 2090/3954; A61B 2090/397; A61B 2090/3983; A61B 2090/3987; A61B 2090/3995; A61B 34/10; A61B 34/20; A61B 90/39
See application file for complete search history.

(56) References Cited

U.S. PATENT DOCUMENTS

2004/0167391 A1*  8/2004  Solar ............... A61B 90/39
                                                     600/426

* cited by examiner

*Primary Examiner* — Mark D Remaly
(74) *Attorney, Agent, or Firm* — Eggink & Eggink; Anthony G. Eggink; Katrina M. Eggink

(57) ABSTRACT

The present disclosure relates to systems and methods to perform a surgical procedure. The systems and methods utilize MRI-compatible fiducial markers including a body having at least one feature configured to receive an MRI-compatible and MRI-visible material and to allow registration of a navigational tool. The MRI-compatible fiducial markers can be affixed to a bone of a patient. The registered navigational tool can be used to advance a surgical tool along a navigational path to perform a surgical procedure.

20 Claims, 14 Drawing Sheets

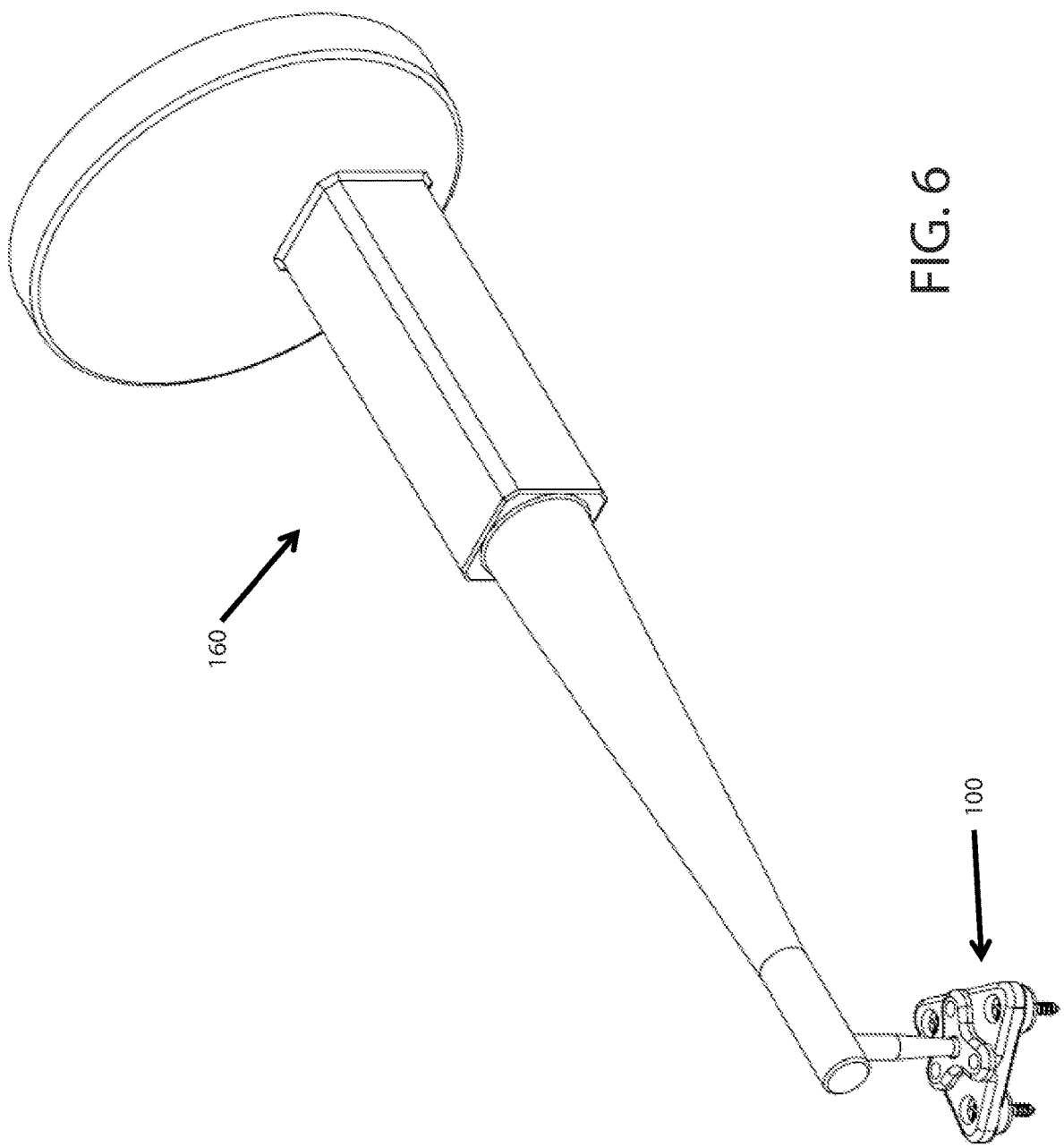

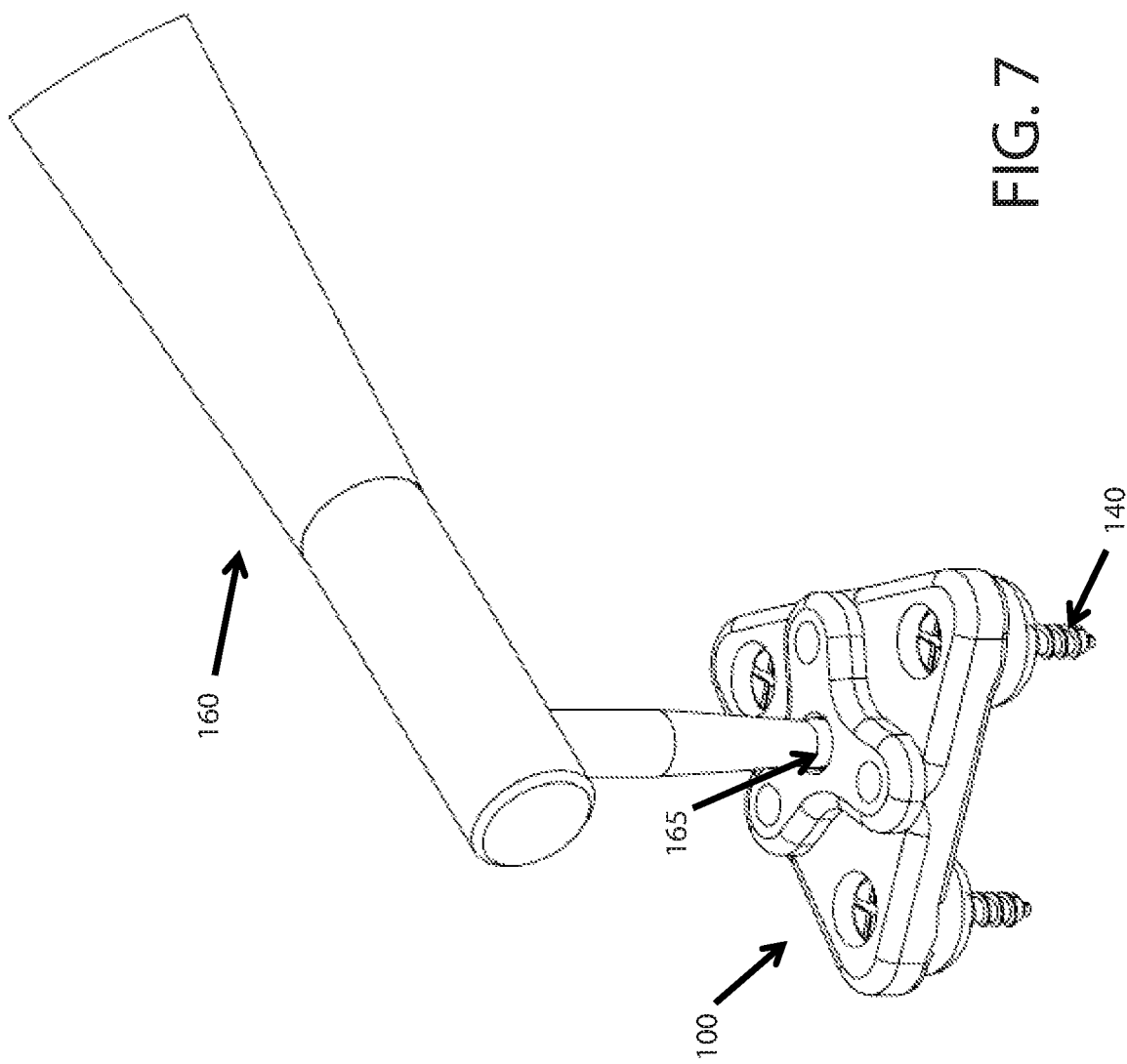

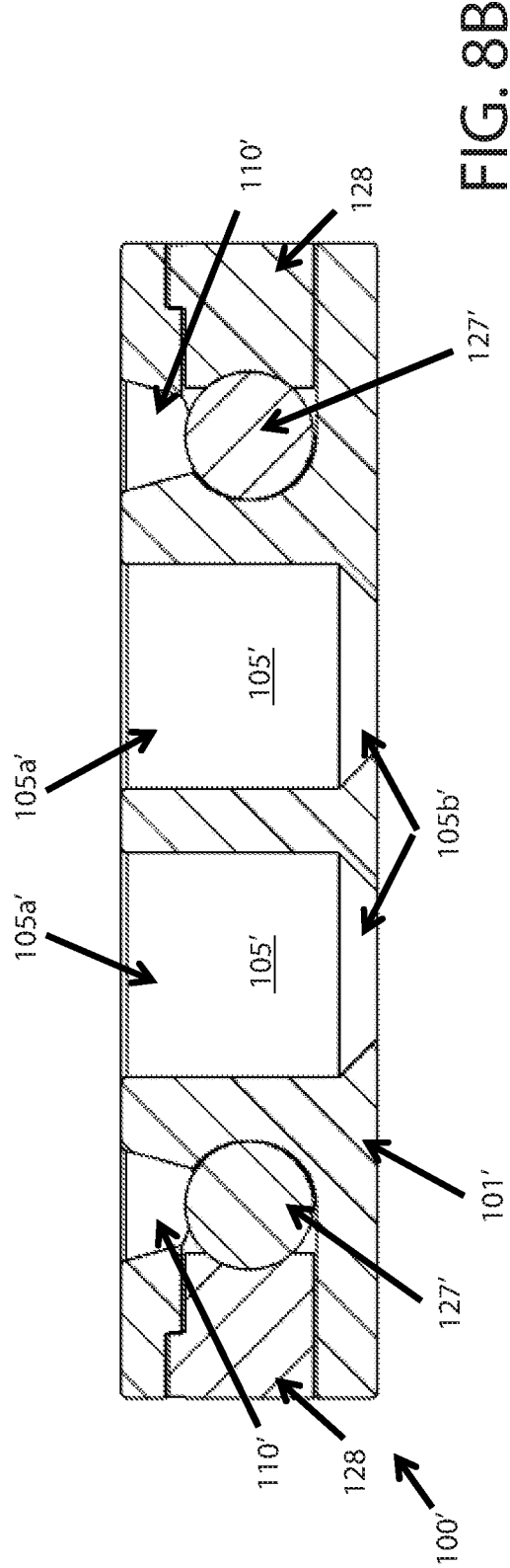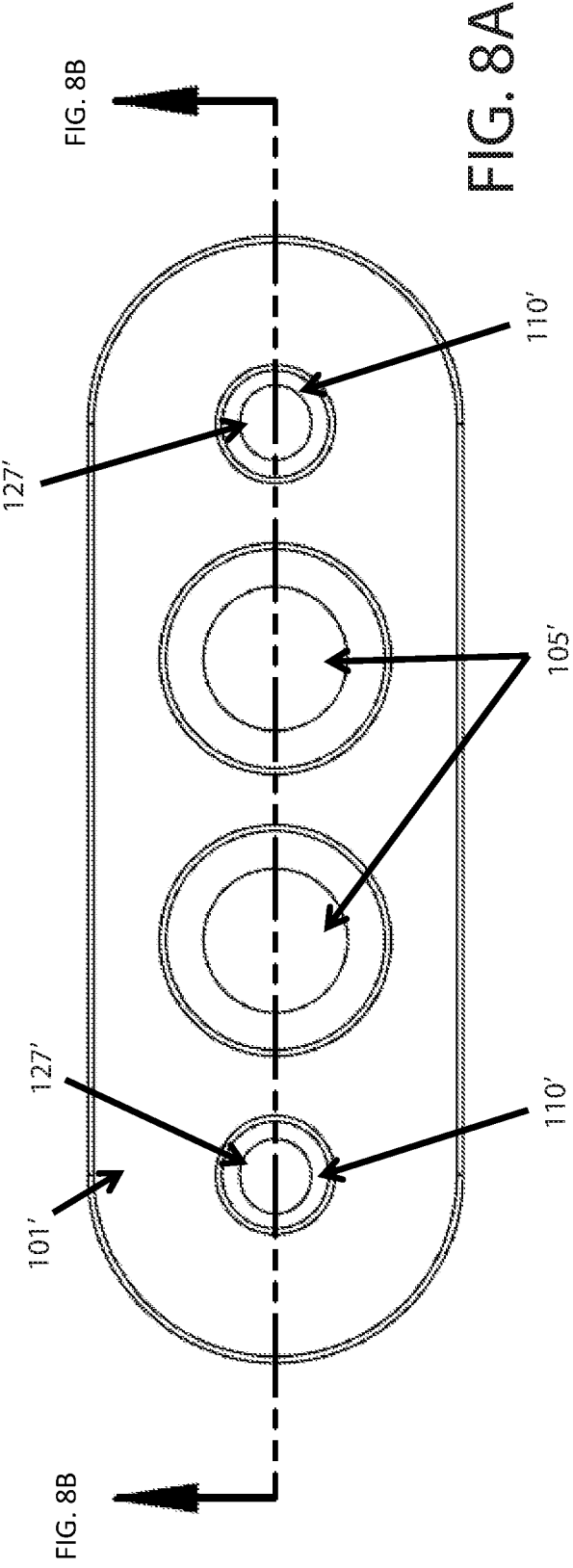

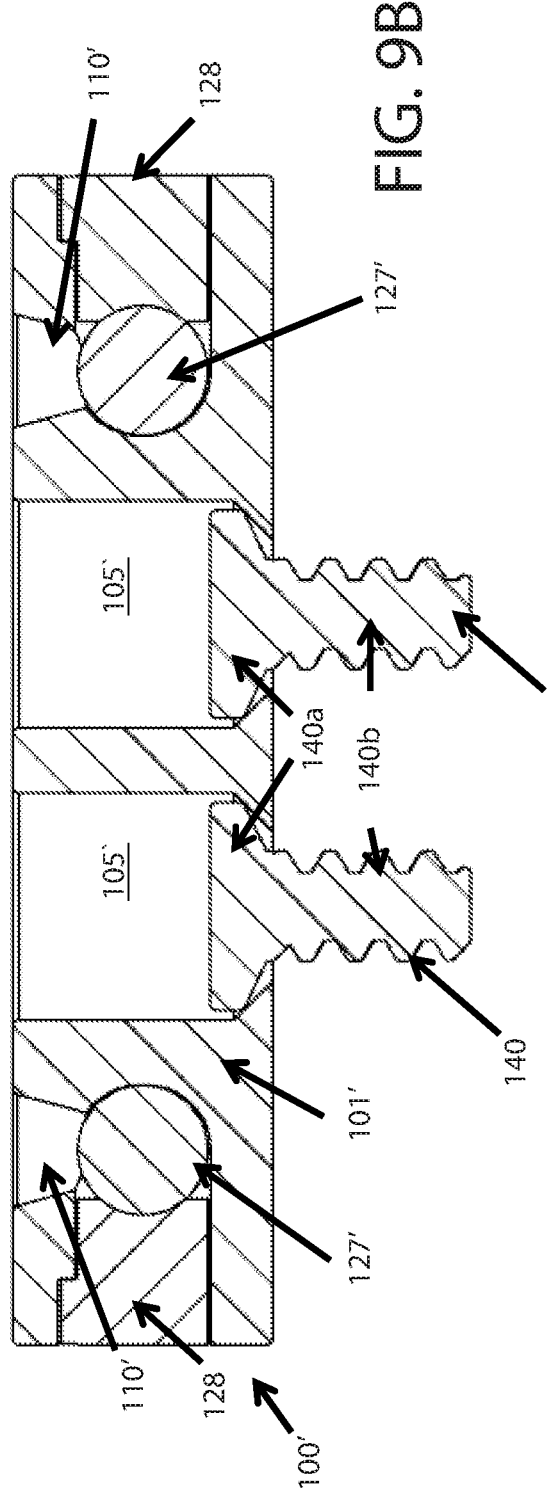
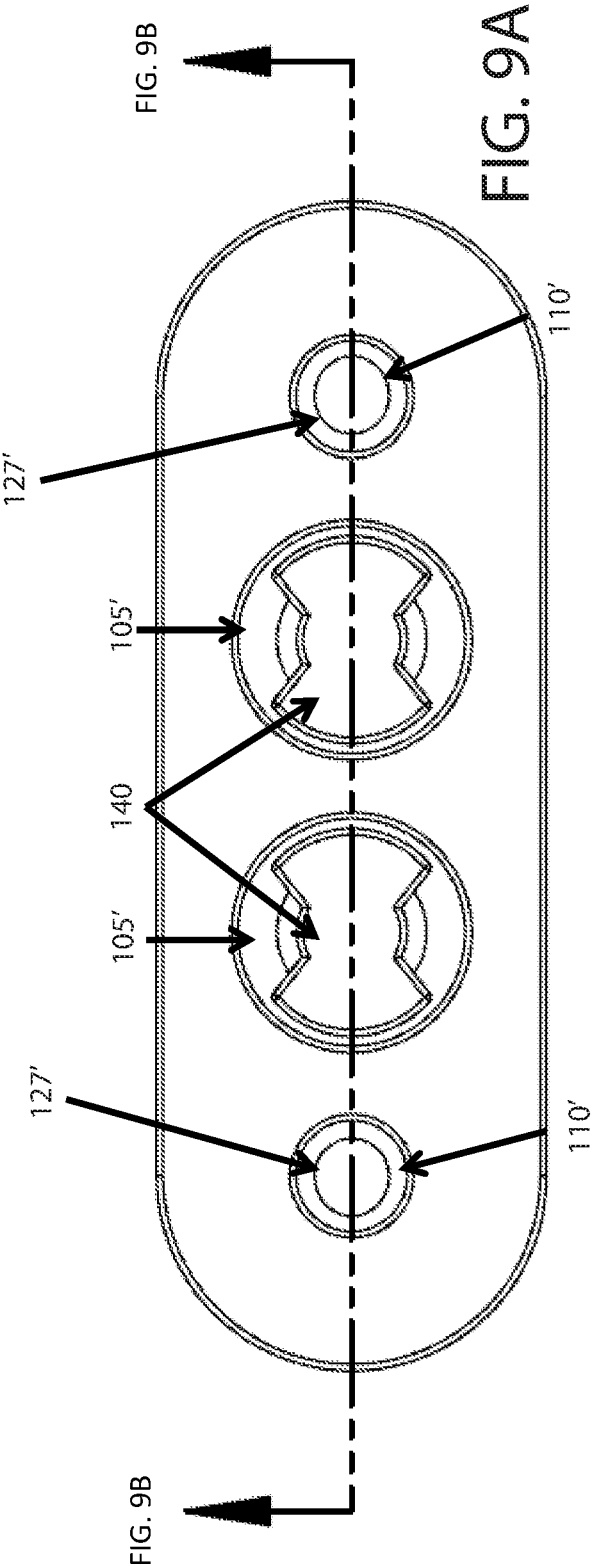

SYSTEMS AND METHODS FOR PERFORMING A SURGICAL PROCEDURE

This Application claims the benefit of U.S. Provisional Patent Application No. 62/715,912 having a filing date of Aug. 8, 2018 and entitled Systems and Methods for Performing a Surgical Procedure and which is incorporated by reference herein.

The present disclosure relates generally to systems and methods for frameless navigation to guide planning and performance of surgical procedures.

When planning and performing a surgical procedure, images are often acquired of the relevant anatomical region of the patient prior to the surgery. These images are used to plan how the procedure will proceed, e.g., where a resection should occur or where probing or stimulation of a brain or muscle should occur. Modern machine-assisted surgery can be used to guide the surgery using the pre-planned navigation path by comparing the location of the surgical instrument in images acquired during the procedure to previously acquired images. A navigational or surgical tool of the machine-assisted surgical instrument is registered in three-dimensional space with the patient and with the imagery acquired previously of the anatomical region of the patient.

To allow co-registration between live images, previously acquired images, and the coordinate system of the navigational tool, fiducial markers that will appear in the images can be placed on the patient. However, fiducial markers that are compatible with multiple imaging modalities (e.g., magnetic resonance imaging and computed tomography) are not available, and therefore, the patient cannot be imaged using the same markers in different types of images. The patient is typically imaged in different imaging modalities during different operations, and the navigational path resulting from such images can suffer from "brain shift."

The present disclosure provides a method of performing a surgical procedure. The method includes selecting a surgical position for a patient in which a surgical procedure will be performed. The method includes affixing at least two magnetic resonance imaging (MRI)-compatible fiducials to a bone of a patient. Each of the MRI-compatible fiducials includes a body having at least one feature including an MRI-compatible and MRI-visible material. The at least one feature allows registration of a navigational tool. Each of the MRI-compatible fiducials includes one or more openings to receive anchors to attach the body to the bone of the patient.

The method comprises acquiring first image volume data representing an anatomical region of a patient and including the at least two MRI-compatible fiducials while the patient is in the selected surgical position. The method includes registering a location of the at least two MRI-compatible fiducials in three-dimensional space by contacting the at least one feature of each MRI-compatible fiducial using the navigational tool. The method includes advancing a surgical tool along a navigational path using the navigational tool. The method includes performing the surgical procedure using the surgical tool.

The present disclosure also provides a magnetic resonance imaging (MRI)-compatible fiducial system. The MRI-compatible fiducial system includes an MRI-compatible fiducial assembly. The MRI-compatible fiducial assembly includes a body including at least one feature configured to receive an MRI-compatible and MRI-visible material. The MRI-compatible fiducial includes one or more openings to receive anchors to attach the body to a bone of a patient. The MRI-compatible fiducial system includes an MRI-compatible and MRI-visible material in the form of a liquid, gel, aqueous solution, or paste to be applied at the at least one feature of the MRI-compatible fiducial before imaging of the MRI-compatible fiducial.

The present disclosure provides a magnetic resonance imaging (MRI)-compatible fiducial marker. The MRI-compatible fiducial marker includes a triangular body, for example. The triangular body includes at least one feature or element to interface with a navigational tool. The at least one feature includes an MRI-compatible and MRI-visible material. The triangular body includes three or more openings configured to receive anchors for securing the fiducial to a bone of a patient. The MRI-compatible fiducial marker includes three bone anchors wherein a portion of each bone anchor is placed through a respective opening from the three or more openings to secure the fiducial to the bone.

The present disclosure provides a magnetic resonance imaging (MRI)-compatible fiducial marker. The MRI-compatible fiducial marker includes a body including at least three features to interface with a navigational tool and allow visualization of the fiducial using MRI. The MRI-compatible fiducial marker includes an MRI-compatible and MRI-visible material that can be placed at or within the at least two features. The MRI-compatible fiducial marker includes at least one opening for receiving a portion of an anchor therethrough to secure the fiducial to a bone. A plane passing through the at least three features does not intersect the anchor when the MRI-compatible fiducial marker is affixed to the bone.

BRIEF DESCRIPTION OF THE DRAWINGS

Reference will now be made to exemplary embodiments, examples of which are illustrated in the accompanying drawings. Wherever possible, the same reference numbers will be used throughout the drawings to refer to the same or like parts. The drawings are not necessarily to scale.

FIG. 6 illustrates a navigational tool interfacing with a fiducial marker in accordance with various embodiments described herein.

FIG. 7 illustrates a detail view of a portion of the navigational tool and fiducial marker of FIG. 6.

FIG. 8A illustrates a top view of a fiducial marker in accordance with various embodiments described herein.

FIG. 8B illustrates a cross-sectional view taken along line FIG. 8B-FIG. 8B of FIG. 8A.

FIG. 9A illustrates a top view of a fiducial marker including anchors in accordance with various embodiments described herein.

FIG. 9B illustrates a cross-sectional view taken along line FIG. 9B-FIG. 9B of FIG. 9A.

DESCRIPTION OF EXEMPLARY EMBODIMENTS

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including" as well as other forms, such as "includes" and "included," is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Computer- or robot-assisted surgical techniques often employ mechanical assist mechanisms that partially or wholly navigate surgical instruments to or within the area of the patient's body that is in need of treatment. Frameless navigation techniques can be used to register the position of the patient relative to the surgical navigation instruments and surgical tools. For proper operation, accurate registration of the tools to the patient is required to avoid causing unintentional damage to surrounding tissues.

For certain types of surgical procedures such as those procedures that require a posterior entry into the brain or procedures involving pediatric patients, conventional methods of registering the surgical navigation system to the patient are inadequate. For example, laser registration is often too inaccurate for posterior entry, for example, into the brain. To overcome these problems, fiducial markers or marker assemblies can be used. After securing the fiducial marker to bone, the patient can be imaged using computed tomography (CT), and the resulting image data can be merged with magnetic resonance imaging (MRI) data within the surgical navigation system. However, the merging of image data from two different imaging techniques can introduce error and requires that the patient be exposed to imaging radiation, which can be undesirable.

Figure 16:
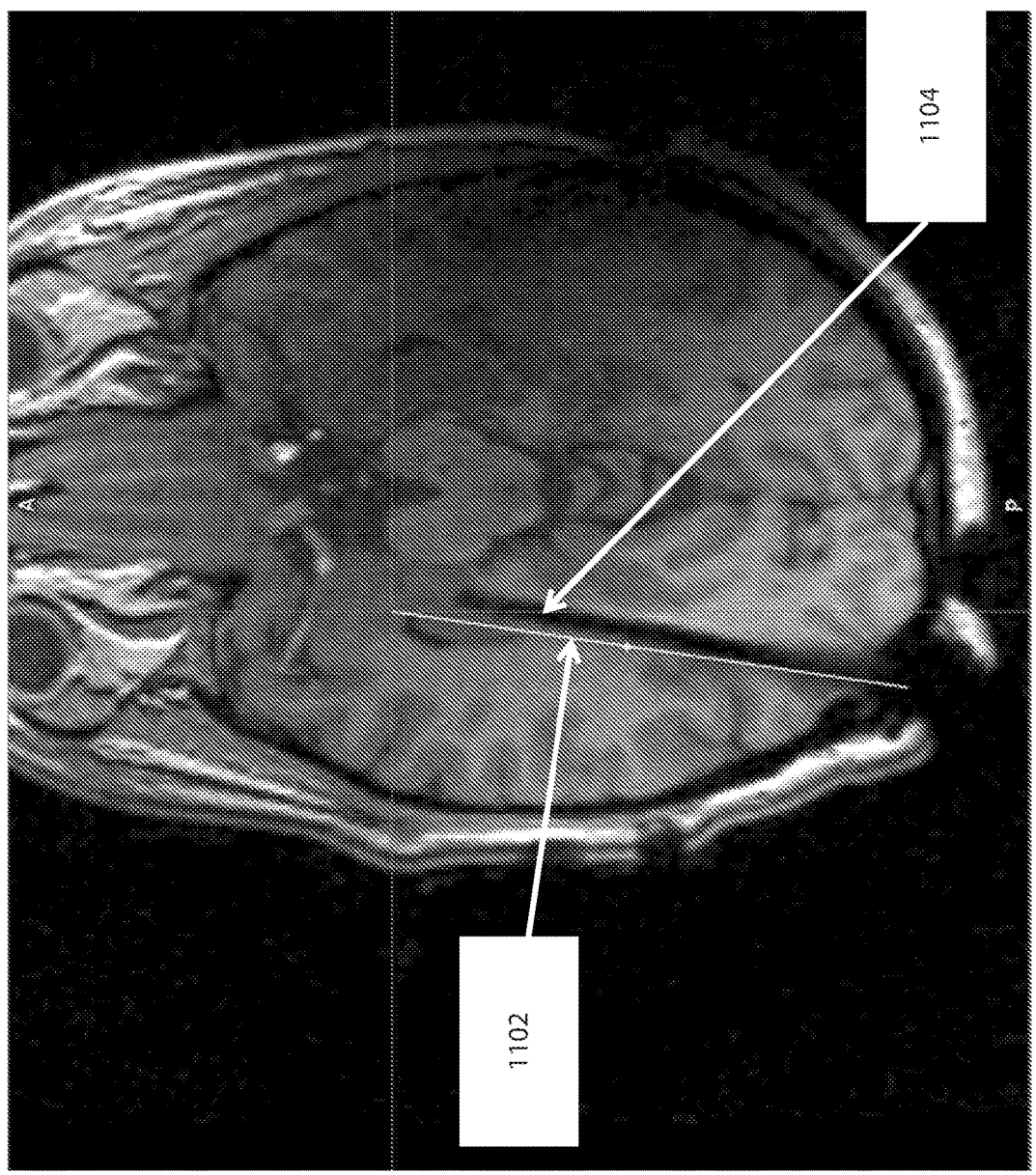
FIG. 16 illustrates the phenomenon of "brain shift" that occurs using conventional navigational planning.

Moreover, the patient may be imaged in different positions during each imaging session during conventional surgical procedure planning and execution. To date, it has often been assumed that pre-operative images accurately reflect the positioning of internal organs, such as the brain, in the patient at the time of the surgical procedure. However, brain structures can shift up to 1.4 centimeters when the patient is moved from a supine to a lateral position. FIG. 16 illustrates a proposed navigational path 1102 developed using MRI imagery acquired when the patient was oriented in a first position. The proposed navigational path 1102 is overlaid upon an MRI image of the patient during the surgical procedure. Due to factors such as brain shift, the actual path 1104 of the tool takes a different trajectory than the proposed navigational path 1102 and terminates at a different end point. The phenomenon of "brain shift" can be exacerbated in some situations by differing positional requirements of different imaging modalities. For example, some instruments may require the patient to be sitting upright during imaging while other instruments require the patient to lie flat.

Systems and methods described herein include an MRI-compatible fiducial marker to allow for imaging of the patient and registration of a navigational tool using MRI image data alone or in combination with data from other imaging modalities. In addition, systems and methods of the present disclosure can enable the patient to maintain a same position for all phases of the surgical procedure including pre-operative imaging, surgical procedure, and post-operative imaging. By maintaining the patient in the same position during all phases of the procedure, problems associated with "brain shift" are avoided as described in greater detail below.

As used herein, "MRI-compatible" refers to a device or material that may be placed into or near a magnetic resonance imaging (MRI) instrument without creating a hazard. In some instances, MRI-compatible devices can consist of materials approved for use in MRI by the United States Food and Drug Administration (FDA), or materials otherwise considered safe for MRI.

As used herein, "MRI-visible" refers to a device or material that has high contrast in an MRI image to enable a viewer to distinguish the MRI-visible device or material from background or surrounding anatomic structures.

FIGS. 1-4 illustrate a perspective view, a top view, a bottom view, and an end view, respectively, of a fiducial marker 100 in accordance with various embodiments described herein. The fiducial marker 100 includes a body 101 having at least one feature 110a, 110h including an MRI-compatible and MRI-visible material 127 to enable visualization using MRI and one or more openings or bores 105 to receive anchors to attach the body 101 to a bone of a patient. The body 101 is shown to have a thickness and generally planar and parallel upper and lower surfaces. The at least one feature 110a, 1101 can interface with a navigational tool to register a position of the fiducial marker 100 in three-dimensional space. The fiducial marker 100 is MRI-compatible. By passing at least a portion of an anchor through each of the one or more openings 105 and into the patient's bone, the fiducial marker 100 can be affixed to the bone of the patient. In some embodiments, the fiducial marker 100 is adapted to be visible in image data acquired using one or more imaging modalities such as MRI or computed tomography (CT). The fiducial marker 100 can be suitable for use in minimally invasive procedures in some embodiments.

The fiducial marker 100 can be adapted to remain affixed to a patient for extended periods (e.g., multiple days). Such longevity is advantageous to allow for direct comparison of data such as images acquired at different times or navigational plans developed using earlier imagery when comparing to newly acquired imagery. For example, first image volume data representing an anatomical region of the patient and including the MRI-compatible fiducials 100 can be acquired while the patient is in a selected surgical position. This first image volume data can be used for navigation planning in some embodiments. The first image volume data can be used in the initial procedure (e.g., electrode placement) in some embodiments. The patient can then leave the operating room and return at a later time to undergo the surgical procedure, which may be a second surgical procedure. During or after the surgical procedure, second image volume data that represents the same anatomical region can be acquired. By leaving the MRI-compatible fiducials 100 in place on the patient, comparison or registration of the first image volume data and the second image volume data is facilitated. Moreover, enabling the fiducial marker 100 to remain affixed to the patient for extended periods facilitates staged surgical procedures (i.e., epilepsy treatment) wherein the same fiducials are used in the different stages of the multi-stage procedure. The same fiducial markers 100 can also be used with intra-operative imaging to assess the completeness of a planned resection or device placement.

The body 101 of the fiducial marker 100 can have a variety of shapes and sizes according to specific needs of the application. In some embodiments, the body 101 can have a circle, oval, star, triangle, square, rectangle, pentagon, hexagon, or other polygon shape. The body 101 can have an irregular shape in some embodiments. In some embodiments, the body 101 does not include sharp edges or corners, the latter having rounded peripheries as shown in the drawings. Avoiding sharp edges promotes the ability of the fiducial marker 100 to remain affixed to the patient over an extended period without fear that the fiducial marker 100 will become snagged or caught on objects in the environment (and thus causing pain to the patient or potentially dislodging the fiducial marker 100). In various embodiments, the body 101 can include an absorbable plate material.

The fiducial marker 100 includes one or more openings 105 to affix or mount the fiducial marker 100 to the patient. For example, the fiducial marker 100 can be affixed to a skull or other bone of the patient. In some embodiments, each opening 105 can include a screw hole. Each opening 105 accepts a portion of an anchor therethrough. In some embodiments, the opening 105 accepts only a body of the anchor or accepts both the body and a head of the anchor in various embodiments. The opening 105 can be a threaded screw hole or a straight-bore through-hole in various embodiments. The opening 105 can be counterbored or countersunk in some embodiments. The counterbore or countersink can include straight sidewalls, spherical/quadratic sidewalls, or angled sidewalls (e.g., cone-shaped). A cross-sectional shape of the opening 105 can be circular, square, polygonal, or other shapes as appropriate. An example geometry for the opening 105 is described in greater detail below with reference to FIG. 5.

The openings 105 can include an upper portion 105a and a lower portion 105b. A diameter, length, or width of the upper portion 105a of the opening 105 can be greater than a diameter, length, or width of the lower portion 105b of the opening 105 in some embodiments. The lower portion 105b is a recessed portion that is below a top surface of the body 101 such that the anchor engages with the lower portion 105b. The lower portion 105b can be sized to allow a shaft of the anchor to pass through but to prevent a head of the anchor from passing through. Thus, the ledge created by the different diameters of the upper portion 105a and the lower portion 105b can engage with the head of the anchor to secure the body 101 of the fiducial marker 100 in position when affixed to the patient.

In some embodiments, the openings 105 can be disposed equidistantly on the body 101. In other words, a distance between adjacent openings 105 can be equal.

In some embodiments, the body 101 includes a raised portion 122, a base 120, and extensions or lower body structures 124. The raised portion or upper body structure 122 can include the features 110a. 110b that include the MRI-compatible and MRI-visible material 127 and that interface with the navigational tool. Anchors 140 made of certain materials (e.g., titanium) can obscure the MRI-compatible and MRI-visible material 127 from certain angles if the material 127 and anchors 140 lie in a same plane. Disposing the features 110a, 110b in the raised portion 122 offsets the features 110a, 111b out of plane with other objects such as anchors that could interfere with imaging of the MRI-compatible and MRI-visible material 127 during an imaging procedure. In some embodiments, the base 120 can have a circle, oval, star, triangle, square, rectangle, pentagon, hexagon, or other polygon shape. The base 120 can have an irregular shape in some embodiments. In some embodiments, the base 120 does not include sharp edges or corners.

The extensions 124 can provide a more stable attachment for the fiducial marker 100 to the bone of the patient. In some embodiments, each opening 105 can pass through one of the extensions 124. If attempting to secure a flat-bottomed marker to the patient without extensions 124, the natural curvature of some locations on the patient (e.g., the skull) creates the possibility of gaps between the base 120 and the patient around the outer edge of the body 101 when the fiducial marker 100 is affixed to the patient. This creates the potential for the fiducial marker 100 to shift or tip (for example, to see-saw along exposed portions of the anchors) and places bending/flexing tension on the body 101 of the marker 100. A bottom surface of each extension 124 contacts the patient and provides a secure attachment at that point due to the smaller surface area of the bottom surface of the extension 124.

The fiducial marker 100 includes feature(s) 110a, 110b to interface with the navigational tool. In some embodiments, the feature 110a, 110b includes at least one of a divot, depression, or opening. In some embodiments, the navigational tool interfaces with the feature 110a, 110b (e.g., the divot) by contacting the feature 110a, 110b. The navigational tool can be interfaced with features 110a, 110b on one or more fiducial markers 100 to orient the navigational tool in three-dimensional space. The interfacing step can be performed simultaneously with all features 110, 110b but is more often performed in sequence to one feature at a time. The navigational tool can be a part of a commercially available frameless navigation system. Commercial systems that may be interfaced with the fiducial markers 100 include the Machine-vision Image Guided Surgery (MvIGS, 7D Surgical, Toronto, Canada), platforms from Stryker Corporation (Kalamazoo, Mich.), platforms from Brainlab AG (Munich, Germany), STEALTHSTATION™ Surgical Navigation system (Medtronic Corporation. Minneapolis, Minn.), and the NEUROBLATE® System (Monteris Medical, Plymouth, Minn.), among others. As an example, the navigational tool can be a probe that interfaces with the feature 110a, 110b of each fiducial marker 100 affixed to the patient to register the navigational tool to those points in space. As another example, the MvIGS system utilizes near continuous high-resolution optical image acquisition (e.g., every eight seconds) to facilitate navigation. By interfacing the MvIGS system with the features 110a, 110b on each fiducial marker 100, the MvIGS system is provided with reference points for 7D optical image navigation to be effective. In some embodiments, the feature 110a, 110b can interface with a probe operatively connected to a ROSA® Brain system (Medtech Surgical Inc./Zimmer Biomet, New York, N.Y.). In some embodiments, the feature 110a, 110b can be located at a center of the fiducial marker 100. For example, the feature 110a, 110b can be located at a center of the top surface of the fiducial marker.

In some embodiments, the feature or element 110a, 110b has a hemispherical shape that secures the navigational tool. In some embodiments, the feature 110a, 110b has an edge that allows the tool to interface with the feature 110a, 110b at angles other than orthogonal. For example, the features 110a, 110b can have a chamfer 131 at the edge. In some embodiments, the features 110a, 110b can have a diameter in a range from 1 mm to 5 mm, 2 mm to 4 mm, 2 mm to 3 mm, or 3 mm to 4 mm. In some embodiments, the diameter can be 3.2 mm. In some embodiments, the diameter can be 2.5 mm. In some embodiments, the features 110a, 110b can have a depth as measured from a top surface of the fiducial marker 100 to the bottom of the feature 110a, 110b in a range from 1 mm to 2 mm, 1.2 mm to 1.8 mm, 1.2 to 1.4 mm, or 1.5 to 1.7 mm. In some embodiments, the depth can be 1.25 mm. In some embodiments, the depth can be 1.6 mm.

Figure 1:
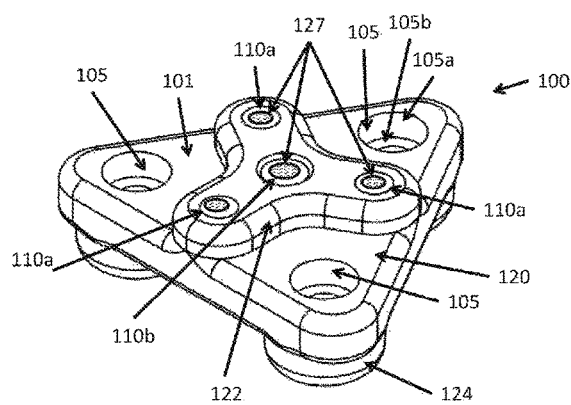
FIG. 1 illustrates a perspective view of a fiducial marker in accordance with various embodiments described herein.

For the fiducial marker 100 shown in FIG. 1, the feature 110a is adapted to interface with a navigational tool available commercially from STRYKER® Corporation. Similarly, the feature 110b is adapted to interface with a navigational tool 160 provided as part of the ROSA® Surgical Robot and Brain available commercially from MedTech SA or platforms from BrainLab AG. An example of the interface between the fiducial marker 100 and the ROSA® system is illustrated in FIG. 6. As shown in FIGS. 1-5, the fiducial marker 100 can include first features 110a and second features 110b in some embodiments wherein the first features 110a interface with a first type of navigational tool and the second features 110b interface with a second type of navigational tool different than the first type. For example, the fiducial marker can include first features 110a to interface with a STRYKER® navigational tool and second features 110b to interface with a ROSA® navigational tool. In some embodiments, the first feature 110a can have a different diameter, depth, or curvature than the second feature 110b.

Figure 2:
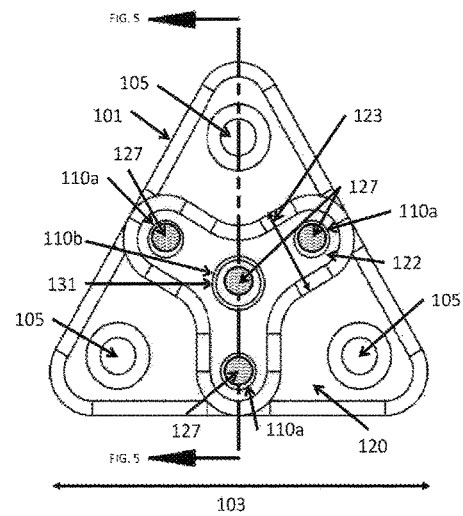
FIG. 2 illustrates a top view of the fiducial marker of FIG. 1 in accordance with various embodiments described herein.
Figure 3:
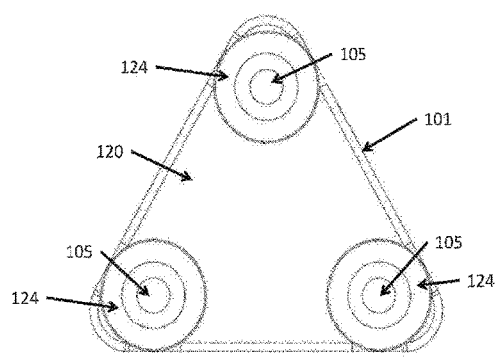
FIG. 3 illustrates a bottom view of the fiducial marker of FIG. 1 in accordance with various embodiments described herein.
Figure 4:
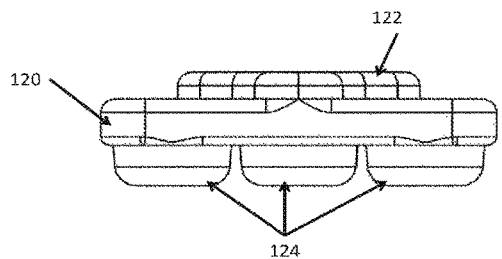
FIG. 4 illustrates an end view of the fiducial marker of FIG. 1 in accordance with various embodiments described herein.

The feature 110a, 110b includes the MRI-compatible and MRI-visible material 127 to enable visualization of the fiducial marker 100 using MRI imaging modalities. In some embodiments, the MRI-compatible and MRI-visible material 127 can include a gel, liquid, aqueous solution, or paste. The gel, liquid, aqueous solution, or paste can be disposed within or on the feature 110a, 110b. For liquid, gel, aqueous solution, or paste materials, exposure to the atmosphere can dry out the material and reduce efficacy of the material for use in MRI visualization. To ensure optimal visualization, the gel, liquid, aqueous solution, or paste can be applied within or on the feature 110a, 110b during the surgical procedure before imaging of the fiducial marker 100. For example, the gel, liquid, aqueous solution, or paste can be applied within or on the feature 110a, 110b immediately before or after affixing the fiducial marker 100 to the patient. In some embodiments, the MRI-compatible and MRI-visible material 127 can include an aqueous component. The MRI-compatible and MRI-visible material 127 can be water soluble. In some embodiments, the MRI-compatible and MRI-visible material 127 can include ultrasound gel. Ultrasound gel provides high contrast in MRI images and is attractive for use in surgical settings because the material is usually already sterile and approved for use in such a setting by regulatory authorities. In some embodiments, the gel, liquid, aqueous solution, or paste can be easily removable from the fiducial device 100 imaging has been completed. For example, the gel, liquid, aqueous solution, or paste can be washed away using water in some embodiments. In some embodiments, the MRI-compatible and MRI-visible material 127 can cover or coat a portion or the entirety of each of the features 110a, 110b. In some embodiments the MRI-compatible and MRI-visible material 127 can be embedded throughout the entire fiducial marker 100. Although the MRI-compatible and MRI-visible material 127 is shown in FIGS. 1 and 2 as having a discrete, self-supporting spheroid shape, the MRI-compatible and MRI-visible material 127 can also form a coating on the features 110a, 110b. In such an embodiment, the MRI-compatible and MRI-visible material 127 can assume a different shape such as that of a hemispherical shell.

In some embodiments, the MRI-compatible and MRI-visible material 127 can include a solid material. The solid material can be an embedded high-MRI contrast material in some embodiments. The MRI-compatible and MRI-visible material 127 can include gold or other metals.

As shown in FIG. 2, the raised portion 122 can have a width 123. In some embodiments, the width 123 of the raised portion 122 can be in a range from 3 mm to 10 mm. In some embodiments, the width 123 of the raised portion 122 can be around 6 mm. The base 120 can have a base width 103. The base width 103 can be in a range from IS mm to 50 mm in various embodiments. In some embodiments, the base width 103 can be 25 mm 2 mm.

Figure 5:
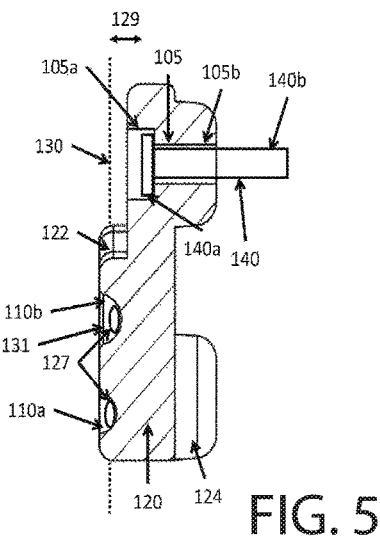
FIG. 5 illustrates a cross-sectional view of the fiducial marker of FIG. 2 taken along line FIG. 5-FIG. 5.

FIG. 5 illustrates a cross-sectional view of the fiducial marker 100 at the cut line indicated in FIG. 2. As shown in FIG. 5, the opening 105 is configured to receive at least a portion of the anchor 140 therethrough to secure the fiducial marker 100 to the patient. The lower portion 105b of the opening 105 can be sized to allow the shaft 140b of the anchor 140 to pass therethrough but to prevent the head 140a of the anchor 140 from passing therethrough. The difference in diameters between the upper portion 105a and the lower portion 105b can be created by counterboring the opening 105 in some embodiments. Contact between the head 140a of the anchor and the ledge created by the differing diameters of the upper portion 105a and the lower portion 105b can provide stabilizing force to the fiducial marker to prevent movement upon fixation of the fiducial marker 100 to the patient.

The anchors 140 can be made of a non-magnetic material in some embodiments. In some embodiments, the anchors 140 can include a resorbable or biodegradable material. The anchors 140 can include plastic or titanium in some embodiments. In some embodiments, the material for the anchors 140 is selected to be compatible with other imaging devices. For example, anchors 140 that include a metal (e.g., titanium) can be compatible with computed tomography (CT) imaging. However, such metal anchors may create artifacts in MRI images thus making them unacceptable for MRI-based navigation. Thus, the fiducial marker 100 could be used to register or overlay images acquired using different imaging modalities based on different aspects of the fiducial marker. For example, the anchors 140 could be imaged using a first modality (i.e., computed tomography) and the MRI-compatible and MRI-visible material 127 can be imaged using a second modality (i.e., MRI). In some embodiments, the anchors 140 can be screws.

The anchors and features can be offset to improve visualization using MRI. For example, in some embodiments, the features 110a, 110b including the MRI-compatible and MRI-visible material 127 can lie in a first plane 130 that does not pass through any anchors 140 when the fiducial marker 100 is affixed to the patient. In other words, the plane 130 passing through the features 110a, 110b does not intersect the anchor 140 when the MRI-compatible fiducial marker 100 is affixed to bone. By offsetting the location of the features 110a, 110b and MRI-compatible and MRI-visible material 127 from other non-homogenous materials in the fiducial marker (e.g., the anchors), the visibility of the MRI-compatible and MRI-visible material 127 in an MRI image is increased. In some embodiments, the fiducial marker 100 can include at least three features 110a, 110b. In some embodiments, a gap 129 exists in a direction parallel to a length of the anchor between the features 110a, 110b and the anchor 140. In some embodiments, the gap 129 exists between the features 110a, 110b and the anchor 140 in a direction perpendicular to a surface of the bone where the anchor is anchored.

FIG. 6 illustrates a navigational tool 160 interfacing with a fiducial marker in accordance with various embodiments described herein, and FIG. 7 illustrates a detail view of a portion of the navigational tool and fiducial marker of FIG. 6. The navigational tool 160 can include an interface end 165 that is adapted to interface with fiducials on the patient. In some embodiments, the feature 110b is sized to interface with the interface end 165 of the navigational tool 160. Fiducial markers 100 described herein are stable enough to withstand pressure from the navigational tool 170 during interfacing and alignment. In particular, embodiments with three openings 105 and three extensions 124 provide a highly stable fiducial marker 100 that distributes the force applied by the navigational tool 170 evenly to the patient. The distribution of force can help prevent injury to the patient.

FIGS. 8A and 8B illustrate a top view and a cross-sectional view, respectively, of a fiducial marker 100' in accordance with various embodiments described herein. The fiducial marker 100' includes a body 101', one or more openings 105' to receive anchors to attach the body 101' to the bone of the patient, and at least one feature 110' including an MRI-compatible and MRI-visible material 12T to enable visualization of the fiducial marker 100' in an MRI image and to interface with the navigational tool. In some embodiments, the fiducial marker 100' can be designed to be used during an open craniotomy for navigation or for hybrid electrode placement.

In accordance with various embodiments, the MRI-compatible and MRI-visible material 127' can include a solid MRI-visible material such as gold. The MRI-compatible and MRI-visible material 127' can include material shaped into a ball or other similar shape. The MRI-compatible and MRI-visible material 127' can be retained at the feature 110' by blocking or constricting any openings in the body 101' to prevent movement of the MRI-compatible and MRI-visible material 127'. For example, the feature 110' can include a tapered opening or cavity in the body 101' that has a diameter that is less than a diameter of the MRI-compatible and MRI-visible material 127'. In some embodiments, the MRI-compatible and MRI-visible material 127' can be loaded into the body 101' through an access opening that is then plugged or closed using a plug 128. The plug 128 can be affixed permanently in position using adhesive or other suitable means of attachment in various embodiments. In some embodiments the MRI-compatible and MRI-visible material 127 can be embedded throughout the entire fiducial marker 100'.

In some embodiments, the MRI-compatible and MRI-visible material 127' can comprise a liquid, gel, paste, or aqueous material as described above with relation to the fiducial marker 100. In such an embodiment, plugs 128 in the body 101' are not needed as the MRI-compatible and MRI-visible material 127' can be added directly through the tapered opening of the feature 110'. In some embodiments, a combination of liquid and solid MRI-compatible and MRI-visible materials 127' can be placed into a same body 101'. In some embodiments, the MRI-compatible and MRI-visible material 127' can be placed into one or more of the openings 105' after the placement of anchors 140.

The tapered opening of the feature 110' can enable a probe or the navigational tool to enter the body 101' to directly contact the MRI-compatible and MRI-visible material 127'. Alternatively, the MRI-compatible and MRI-visible material 12T can be encapsulated by the body 101' in some embodiments. Encapsulating the material 127' can enable provision of the MRI-compatible and MRI-visible material 127' at the time of manufacture of the fiducial marker 100, 100' while preventing the material 127' from drying out or leaking. In some embodiments, the encapsulated material 127 can be separated from a surface of the body 101 by a thin wall to allow the navigational tool to approach the material 127 as closely as possible.

FIGS. 9A and 9B illustrate a top view and a cross-sectional view, respectively, of the fiducial marker 100' including anchors 140 in accordance with various embodiments described herein. The openings 105' in the fiducial marker 100' can include the top portion 105a' and the bottom portion 105b'. The head 140a of the anchor 140 can engage with the bottom portion 105b' of the opening 105' to secure the fiducial marker 100' to the bone of the patient. In accordance with various embodiments, the bottom portion 105b' or a transition from the top portion 105a' to the bottom portion 105b' can be tapered to produce a countersink. The head 140a of the anchor 140 can include a tapered section that engages with the countersink to increase the surface area between the anchor 140 and walls of the opening 105'.

Figure 10:
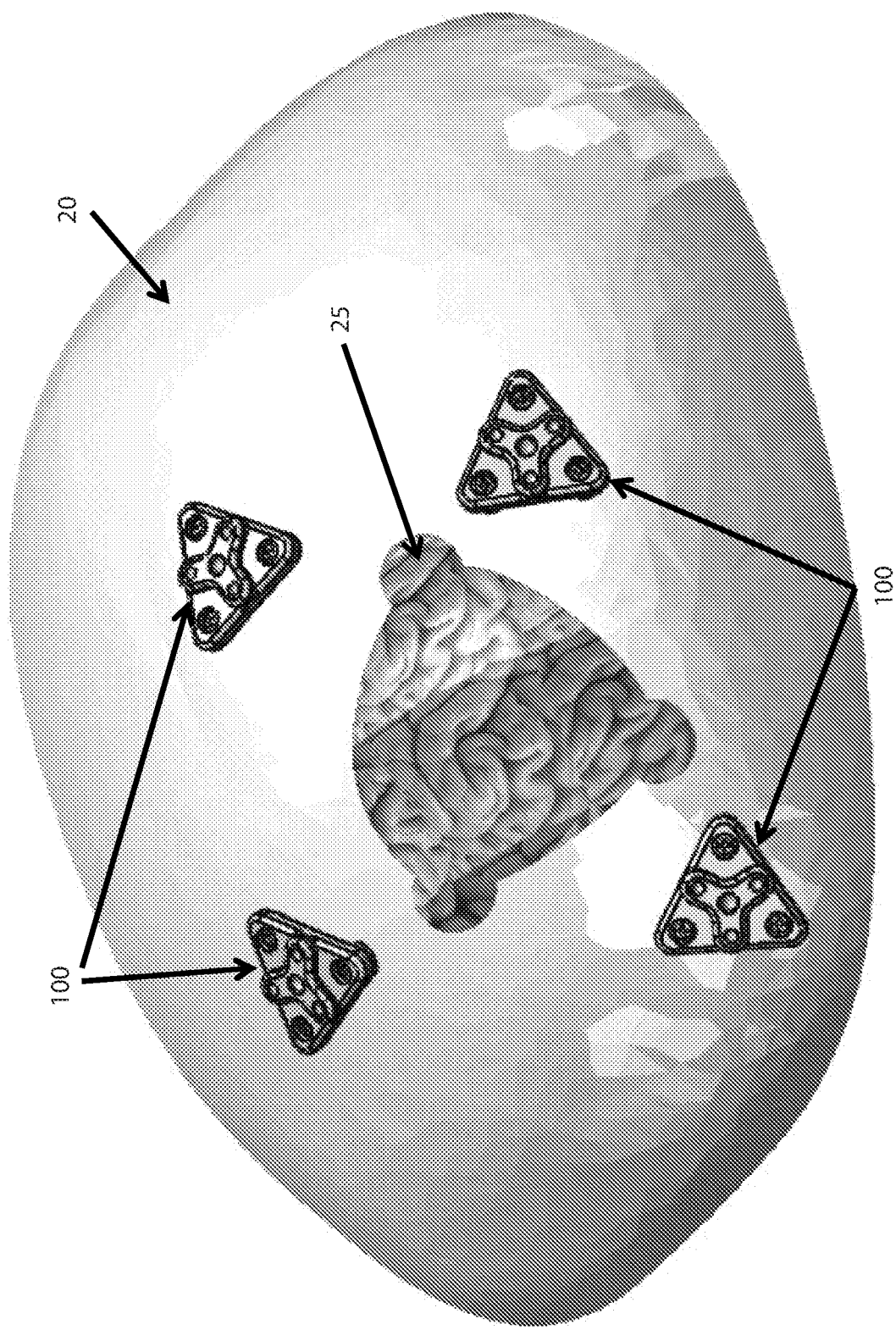
FIG. 10 illustrates MRI-compatible fiducial markers affixed to a skull in accordance with various embodiments described herein.
Figures 10A, 10B:
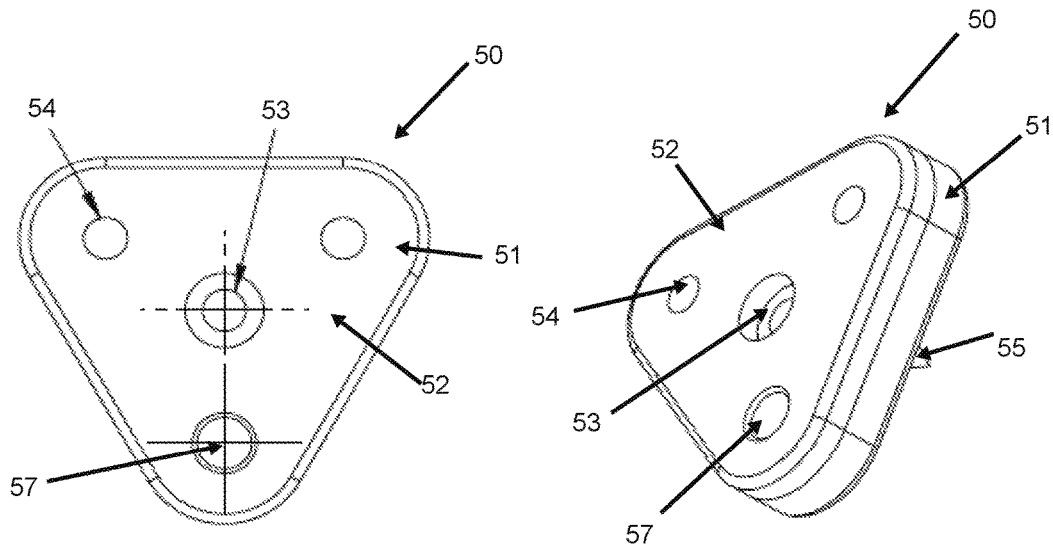
FIG. 10a-10e are top plan, top perspective, lateral plan, bottom plan and bottom perspective views respectively of another embodiment of the invention.
Figures 10C, 10D, 10E:
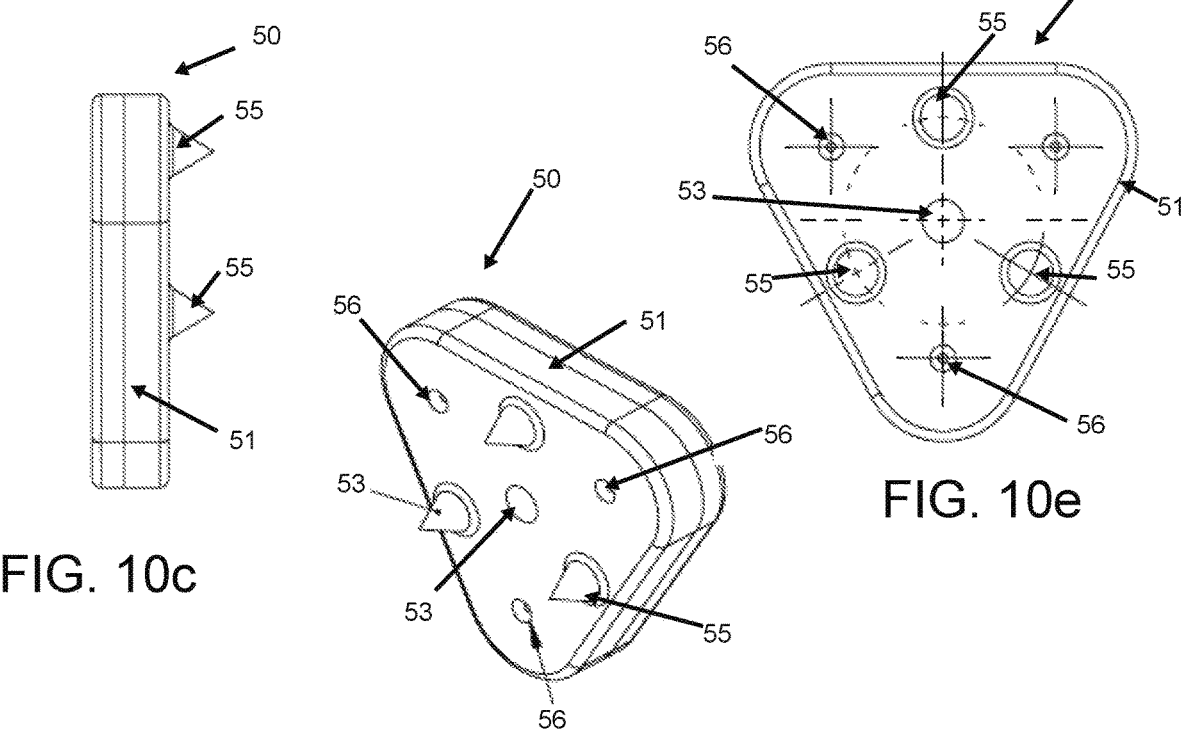

Referring to FIGS. 10a-10c, an embodiment of the fiducial marker assembly 50 is shown having body structure 51 with a securement hole 53 and tool registration points 54 and 57 in the body top portion 52. Spike members 55 are shown extending from the bottom 58 of the body structure 51 to secure the fiducial marker assembly 50 in place subsequent the extension and placement of a screw through securement hole 53. The spike members 55 stabilize the body structure 51 and prevent any rotation, for example. The tool registration points 54 and 57 are shown to have different diameters thereby permitting the registration of different surgical tools. The registration points are further shown to be aligned with fill holes 56 in the body bottom portion for the insertion or placement of the MRI-compatible and MRI-visible material.

Referring to FIGS. 11a-11e, an embodiment of the fiducial marker assembly 60 is shown having body structure 61 with securement holes 63 which extend through extensions 67. Registration points 64 and 65 are shown as indentations in body top portion 62 and which are adapted to receive different surgical tools. The fill holes 68 shown on the bottom 66 of fiducial marker body 61 are constructed to receive the MRI-compatible and MRI visible material and are aligned with the registration points 64 and 65 on the top of the body structure 61. The extensions 67 and securement holes 63 permit the securement of the body structure 61 as further discussed with respect to FIGS. 1-5 above.

FIG. 10 illustrates MRI-compatible fiducial markers 100 affixed to a skull 20 in accordance with various embodiments described herein. In accordance with various embodiments described herein, registration of a navigational tool can be made by contacting the tool to one MRI-compatible fiducial marker, two MRI-compatible fiducial markers, three MRI-compatible fiducial markers, four MRI-compatible fiducial markers, five MRI-compatible fiducial markers, or any number of MRI-compatible fiducial markers to meet application-specific requirements for accuracy or reliability. The MRI-compatible fiducial markers 100 can be affixed to bone that overlays unaffected tissue in some embodiments. The markers 100 can be arranged to substantially surround a surgical access point 25 such as a hole in the skull 20.

Figure 11A:
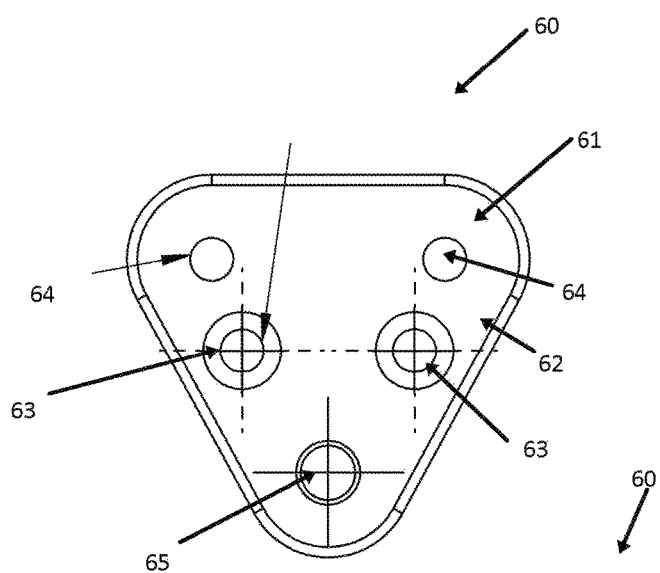
FIG. 11a-11e are top plan, top perspective, lateral plan, bottom plan and bottom perspective views respectively of another embodiment of the invention.
Figure 11B:
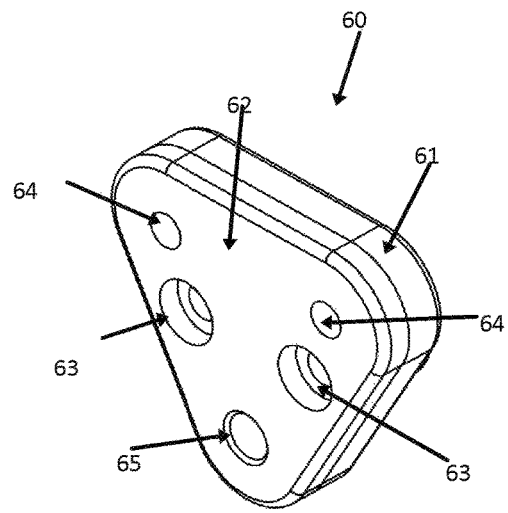
Figure 11C:
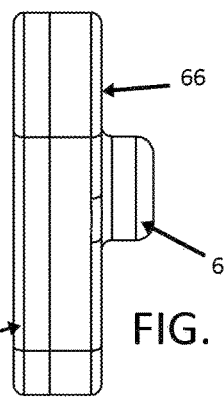
Figure 11D:
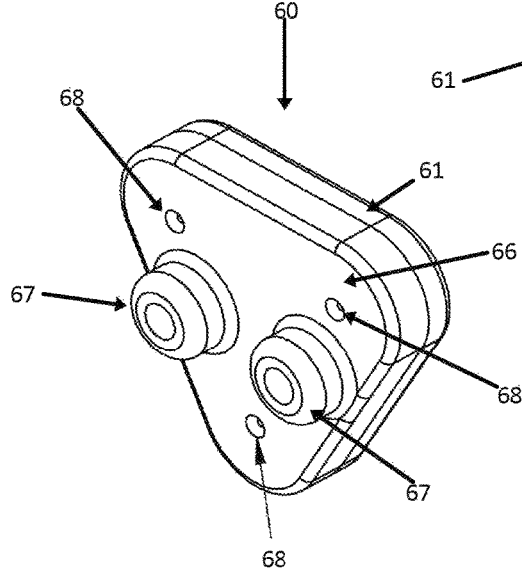
Figure 11E:
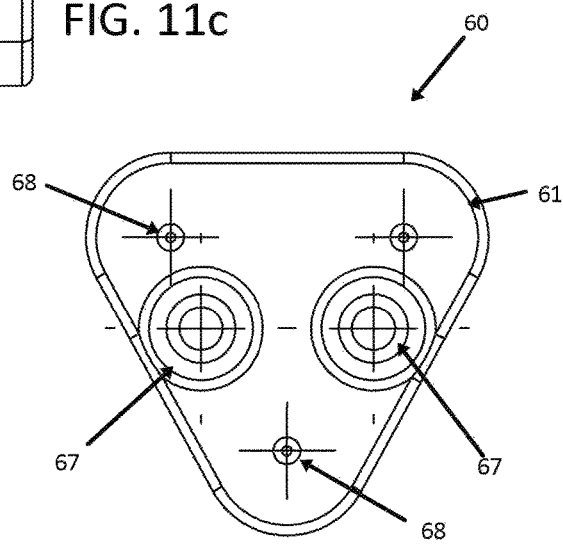
Figure 11:
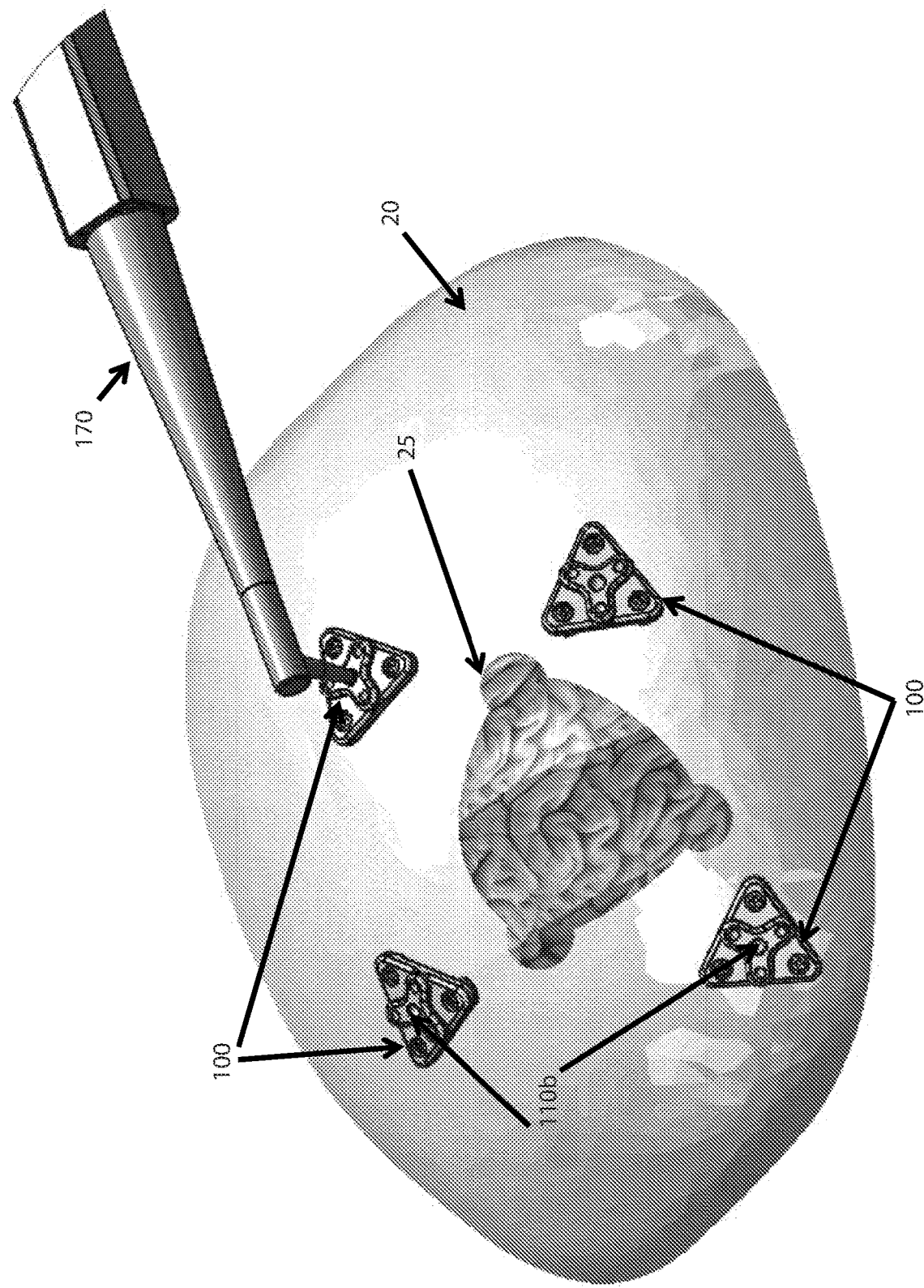
FIG. 11 illustrates registration of a navigational tool to MRI-compatible fiducial markers affixed to the skull in accordance with various embodiments described herein.
Figure 12:
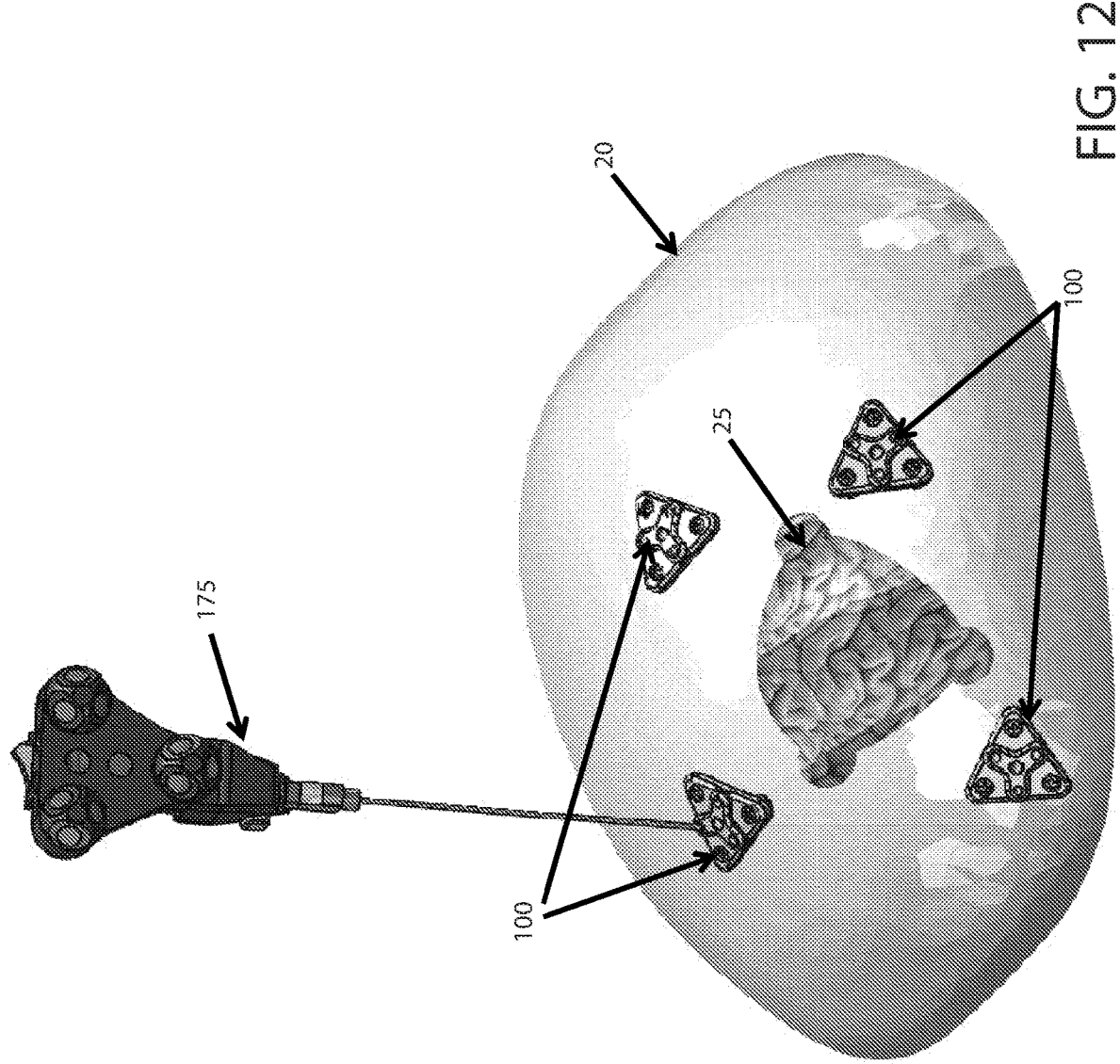
FIG. 12 illustrates registration of a navigational tool to MRI-compatible fiducial markers affixed to the skull in accordance with various embodiments described herein.

FIG. 11 illustrates registration of the navigational tool 170 to MRI-compatible fiducial markers affixed to a skull in accordance with various embodiments described herein. In the illustration, the navigational tool 170 associated with the ROSA® system is shown. The navigational tool 170 interfaces with the feature 110b of each MRI-compatible fiducial marker to register the location of the navigational tool 170 with respect to the patient in three-dimensional space. FIG. 12 illustrates registration of a navigational tool 175 to MRI-compatible fiducial markers affixed to a skull in accordance with various embodiments described herein. In the illustration, the navigational tool 175 associated with the STRYKER® navigation system is shown. The navigational tool 175 interfaces with the features 110a of each MRI-compatible fiducial marker 100 to register the location of the navigational tool 175 with respect to the patient in three-dimensional space.

Figure 13:
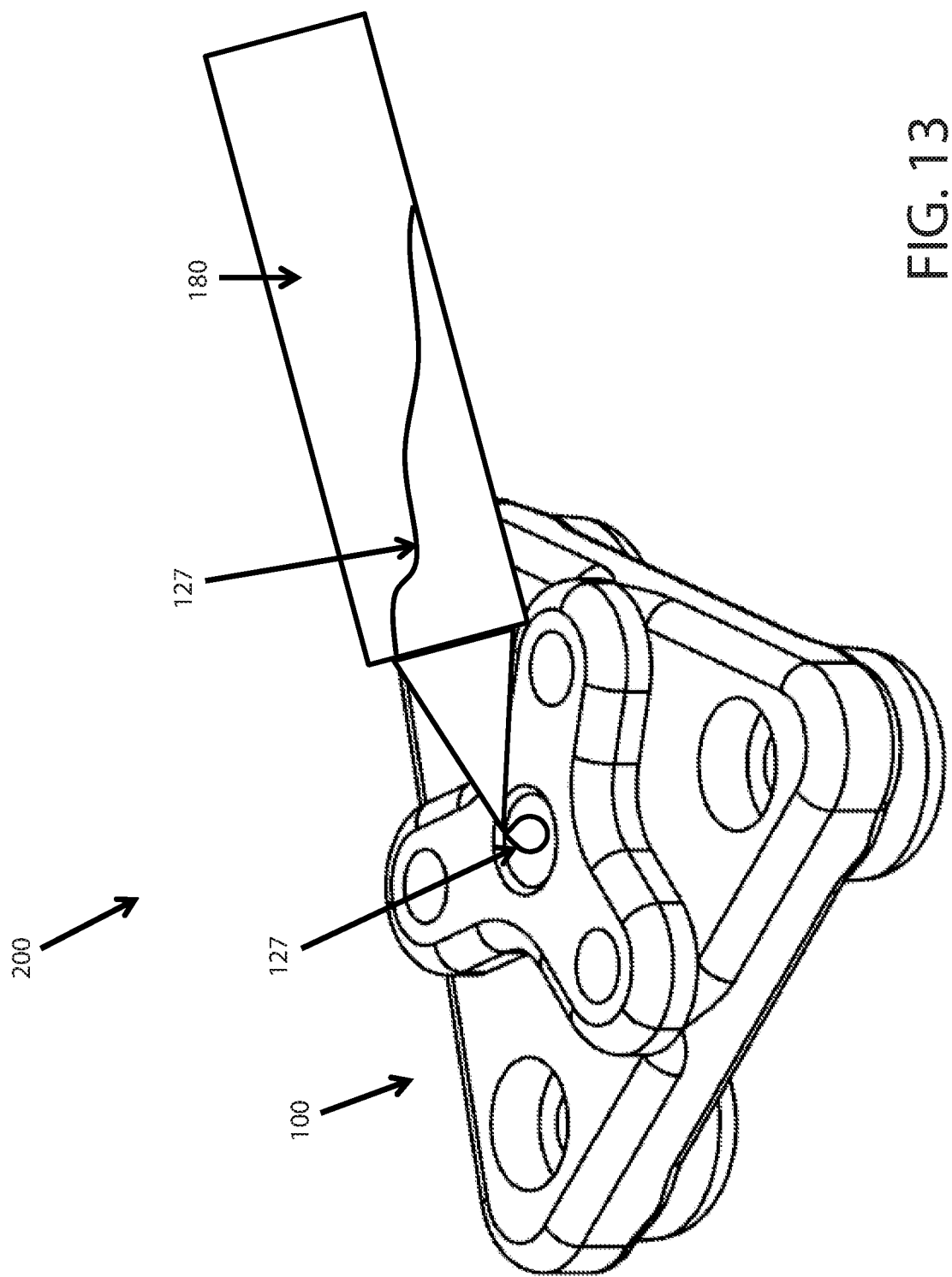
FIG. 13 illustrates an MRI-compatible fiducial system in accordance with various embodiments described herein.

FIG. 13 illustrates an MRI-compatible fiducial system 200 in accordance with various embodiments described herein. The MRI-compatible fiducial system 200 includes the MRI-compatible fiducial marker 100, 100' and the MRI-compatible and MRI-visible material 127 in the form of a liquid, gel, aqueous solution, or paste. The MRI-compatible and MRI-visible material 127 can be applied at the at least one feature 110a, 110b, 110' of the MRI-compatible fiducial 100, 110' before imaging of the MRI-compatible fiducial 100, 100'.

In some embodiments, the fiducial system 200 can include a container 180 to dispense the MRI-compatible and MRI-visible material 127 onto the MRI-compatible fiducial 100, 100'. For example, the container 180 can include a plastic squeeze bottle, syringe, or other dispensing structure. The container 180 and one or more fiducials 100, 100' can be provided as a kit including instructions to first attach the fiducial 100, 100' at the appropriate location on the patient and then to apply the MRI-compatible and MRI-visible material 127 to the fiducial 100, 100' at the one or more features 110a, 110b, 110'.

In some embodiments, the MRI-compatible and MRI-visible material 127 in the form of a liquid, gel, aqueous solution, or paste can include an aqueous component. The MRI-compatible and MRI-visible material 127 can be water soluble. In some embodiments, the MRI-compatible and MRI-visible material 127 can include ultrasound gel. Ultrasound gel provides high contrast in MRI images and is attractive for use in surgical settings because the material is usually already sterile and approved for use in such a setting by regulatory authorities. In some embodiments, the gel, liquid, aqueous solution, or paste can be easily removable from the fiducial device 100 imaging has been completed. For example, the gel, liquid, aqueous solution, or paste can be washed away using water in some embodiments.

Figure 14:
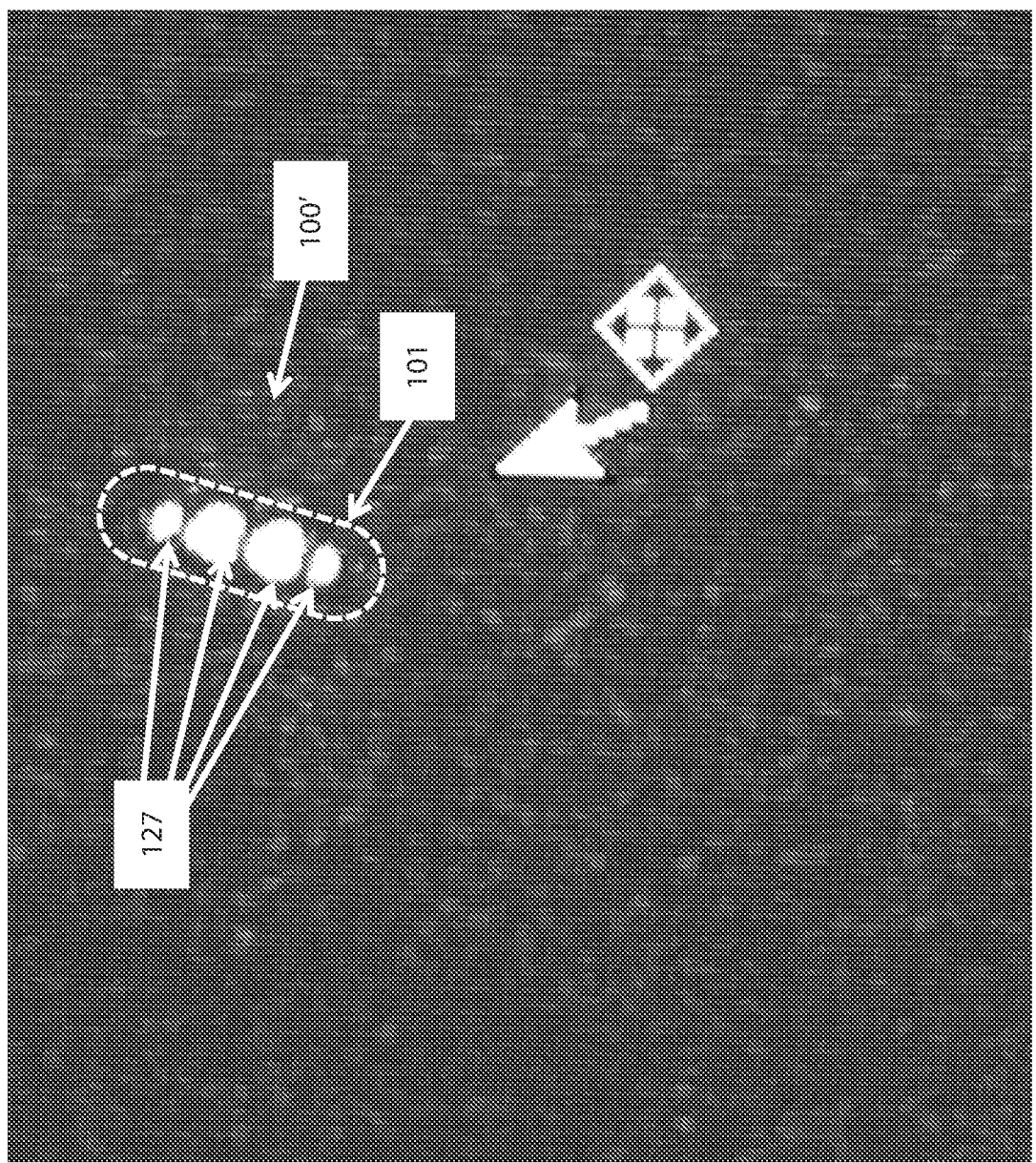
FIG. 14 is an image of the fiducial marker of FIGS. 8A-9B acquired using magnetic resonance imaging in accordance with various embodiments described herein.

FIG. 14 is an image of the fiducial marker 100' acquired using magnetic resonance imaging in accordance with various embodiments described herein. In this example, the MRI-compatible and MRI-visible material 127 was placed at the two openings 105 and at the two features 110' of the fiducial marker 100' as shown in the embodiment of FIGS. 8A-9B. Because the body 101 and anchors 140 are constructed from an MRI inactive material in this example, they do not appear in the MRI image. The MRI-compatible and MRI-visible material 127 is clearly visible in the MRI image.

Figure 15:
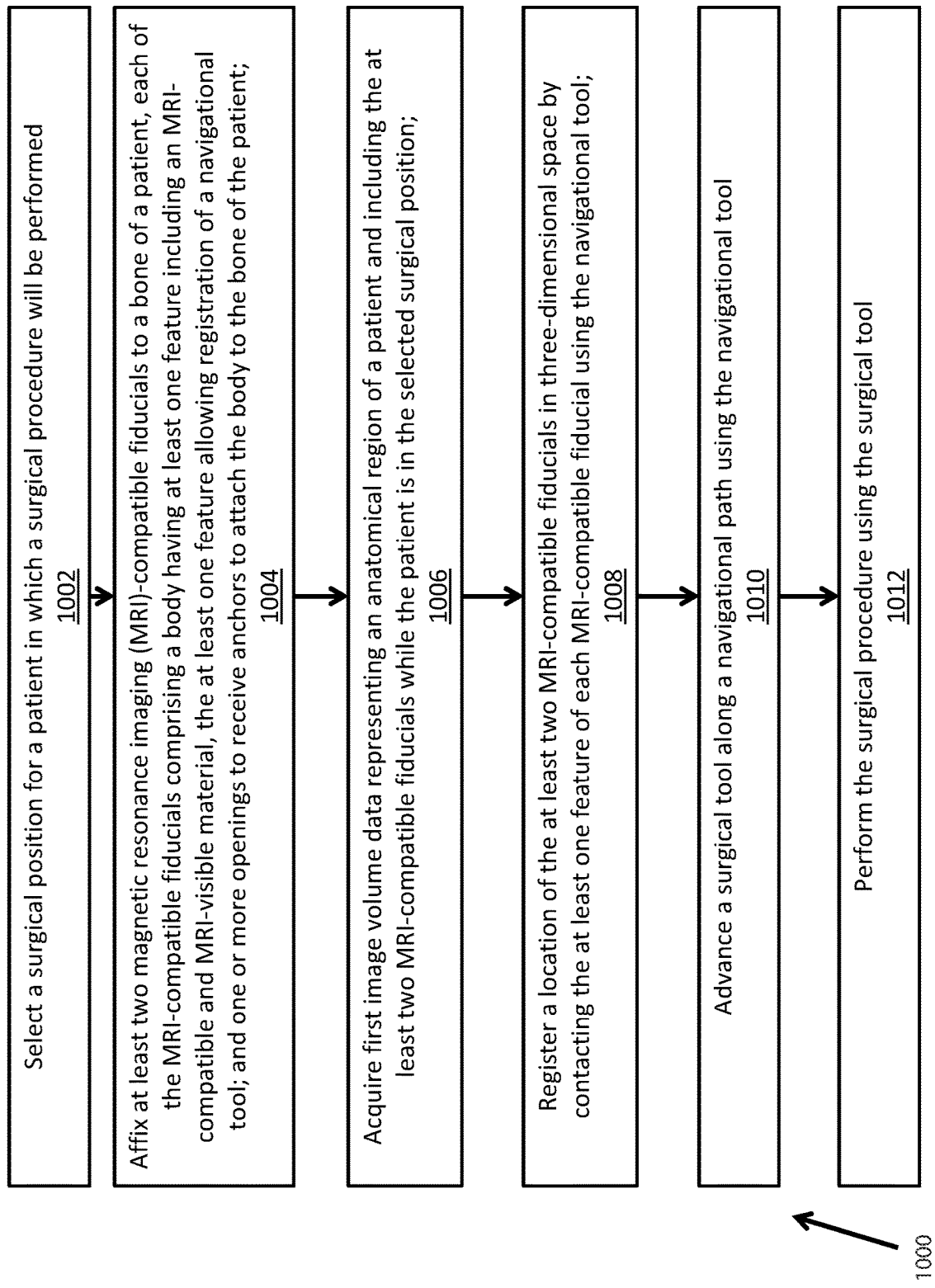
FIG. 15 illustrates a flowchart for a method of performing a surgical procedure in accordance with various embodiments of the present application.

FIG. 15 illustrates a flowchart for a method 1000 of performing a surgical procedure in accordance with various embodiments of the present application. The method 1000 includes selecting a surgical position for a patient in which a surgical procedure will be performed (step 1002). In various embodiments, the surgical position can include a prone position, a supine position, a lateral position, a Fowler's position, or a Trendelenberg position. In some embodiments, the surgical position can be an irregular, non-standard, or unconventional position. In various embodiments, the surgical procedure can include at least one of stereotactically implanting an electrode within a portion of a brain of the patient, resection of an organ of the patient (e.g., brain), delivery of radiation to a portion of the brain of the patient, delivery of focused ultrasound waves to a portion of the brain of the patient, placement of a laser fiber into the brain of the patient, deep brain stimulation (DBS), stereoelectroenccphalography (sEEG), neurostimulation (e.g., using the RNS® system), coordination of stereotactic radiosurgery, stereotactic focused ultrasound, transcranial magnetic stimulation (TMS), or laser interstitial thermal therapy (LITT).

The method 1000 includes affixing at least two MRI-compatible fiducial markers 100, 100' to a bone of the patient (step 1004). Each of the MRI-compatible fiducial markers 100, 100' includes the body 101 having at least one feature 110a, 110b, 110' including an MRI-compatible and MRI-visible material 127. The features 110a, 110b, 110' allows registration of a navigational tool such as the navigational tool 170 from the ROSA® system. The fiducial markers 100, 100' include one or more openings 105 to receive anchors 140 to attach the body 101 to the bone of the patient.

The method 1000 includes acquiring first image volume data representing an anatomical region of the patient and including the at least two MRI-compatible fiducial markers 100, 100' while the patient is in the selected position (step 1006). For example, the first image volume data can include imaging data acquired through MRI, CT, PET, or other suitable imaging technologies. The method 1000 includes registering a location of the at least two MRI-compatible fiducial markers 100, 100' in three-dimensional space by contacting the at least one feature of each MRI-compatible fiducial using the navigational tool 170 (step 1008). For example, the navigational tool 170 can sequentially contact each feature 110a, 110b, 110' of each MRI-compatible fiducial marker 100, 100'. By contacting each feature, the relative location of the navigation tool 170 with respect to the fiducial markers 100, 100' becomes known. It is then subsequently possible to register the location of the navigational tool 170 in space in image volume data that include the fiducial markers 100, 100'.

The method 1000 includes advancing the surgical tool along a navigational path using the navigational tool 170 (step 1010). For example, the surgical tool can include a laser emitter, an electrode, an imaging instrument, a heating element, or any other suitable tool to perform a surgical procedure. The navigational path can be determined using the first image volume data in some embodiments. The navigational path can include a path from the exterior of the patient to the problem center in the patient's body to be treated. In some embodiments, the navigational path can be selected or planned to avoid contacting risk structures. For example, the navigational path for a procedure to target a portion of the brain might be planned to avoid crossing risk structures such as the optic nerve and speech specific cortex. The method 1000 includes performing the surgical procedure using the surgical tool (step 1012). For example, an electrode can be used as a surgical tool to perform a DBS therapy on the patient.

In some embodiments, the method 1100 can include acquiring second image volume data representing the anatomical region of the patient after or during the surgical procedure while the patient is in the selected surgical position. The first image volume data can be compared to the second image volume data to assess whether the surgical procedure was successful. The second image volume data can include at least one of CT or MRI data. If the surgical procedure (e.g., resection) is considered unacceptable after acquisition of the second image volume data, further surgical procedures may be performed followed by additional acquisition of image volume data until the results of the collective surgical intervention are satisfactory.

Although the systems and methods presented herein are described with respect to surgical procedures on the brain, use of the systems and methods presented herein is not limited to brain or head procedures. In some embodiments, the fiducial markers 100 can be attached to bones in other areas of a patient including, but not limited to, bones in the thorax, arms, legs, feet, hands, or hip region.

Other embodiments will be apparent to those skilled in the art from consideration of the specification and practice of this disclosure. It is intended that the specification and examples be considered as exemplary only, with the true scope and spirit of the disclosed devices and methods being indicated by the following claims.

That which is claimed is:

1. An MRI compatible fiducial assembly comprising:
  a) a predetermined shaped body having a planar upper surface, a thickness and a planar lower surface generally parallel said planar upper surface;
  b) a plurality of formed cavities extending into said shaped body;
  c) at least one bore extending through said shaped body, said bore adapted to receive an MRI compatible bone anchor; and
  d) an MRI-compatible and MRI-visible material for insertion in each of said formed cavities and being adapted for navigational tool registration.

2. The MRI compatible fiducial assembly of claim 1, wherein said shaped body has a raised body structure being unitary with and extending upward said upper surface of said shaped body and wherein said formed cavities are located in said upper body structure of said shaped body and wherein said at least one bore extends through said upper surface of said shaped body.

3. The MRI compatible fiducial assembly of claim 1 wherein said plurality of formed cavities include cavities of different sizes adapted for the registration of different navigational tools and wherein said shaped body has at least one lower body extending downward front said lower surface of said shaped body.

4. The MRI compatible fiducial assembly of claim 1, wherein said shaped body is selected from the group of shapes consisting of a circle, oval, triangle, square, rectangle, pentagon, hexagon, other polygon shape and an irregular shape.

5. The MRI compatible fiducial assembly of claim 1, wherein said shaped body has a rounded periphery and wherein said shaped body has a width ranging between 15 mm-50 mm.

6. The MRI compatible fiducial assembly of claim 5, wherein said shaped body is triangular.

7. The MRI compatible fiducial assembly of claim 1, wherein said MRI-compatible and MRI-visible material is selected from the group of materials consisting of a liquid, a gel, an aqueous solution, a material including an aqueous component, a paste and a solid.

8. The MRI compatible fiducial assembly of claim 1, wherein at least one spike shaped structure extends downward from said bottom surface.

9. The MRI compatible fiducial assembly of claim 2, wherein a plurality of fiducial assembles form a system for a surgical procedure.

10. An MRI compatible fiducial assembly comprising:
  a) a shaped body having an upper surface, a thickness and a lower surface generally parallel said upper surface, said shaped body having at least one lower body extending from said lower surface;
  b) a raised body structure extending upward from said upper surface of said shaped body;
  c) a plurality of formed cavities extending into said raised body structure of said shaped body;
  d) a bore extending through said shaped body, said bore adapted to receive an MRI compatible bone anchor; and
  e) an MRI-compatible and MRI-visible material for insertion in said formed cavities.

11. The MRI compatible fiducial assembly of claim 10, wherein a plurality of assemblies are provided to substantially surround a surgical access point.

12. The MRI compatible fiducial assembly of claim 10, wherein said shaped body and said raised body structure have rounded peripheries, wherein said shaped body has a width ranging between 15 mm and 50 mm and wherein said raised body structure has a width ranging between 3 mm and 10 mm.

13. The MRI compatible fiducial assembly of claim 10, wherein said MRI-compatible and MRI-visible material is selected from the group of materials consisting of a liquid, a gel, an aqueous solution, a material including an aqueous component, a paste and a solid.

14. The MRI compatible fiducial assembly of claim 10, wherein said plurality of formed cavities include cavities of two different predetermined sizes adapted ter the registration of different navigational tools.

15. The MRI compatible fiducial assembly of claim 10, wherein said shaped body and said raised body structure are triangular structures, wherein a lower body extends from said lower surface of said shaped body and wherein three bores are provided and positioned at each apex of said triangle structure of said shaped body.

16. An MRI compatible fiducial assembly comprising:

a) a shaped body having an upper surface, a thickness and a lower surface, a raised body structure extending upward from said upper surface of said shaped body, said shaped body and said raised body having rounded peripheries;

b) a plurality of formed cavities extending into said raised body of said shaped body, said plurality of formed cavities including cavities of two different predetermined sizes adapted for the registration of different navigational tools;

c) a bore extending through said shaped body, said bore adapted to receive an MRI compatible bone anchor; and d) an MRI-compatible and MRI-visible material for insertion in said formed cavities.

17. The MRI compatible fiducial assembly of claim 16, wherein a plurality of assemblies are provided to substantially surround a surgical access point.

18. The MRI compatible fiducial assembly of claim 16, wherein said MRI-compatible and MRI-visible material is selected from the group of materials consisting of a liquid, a gel, an aqueous solution, a material including an aqueous component, a paste and a solid.

19. The MRI compatible fiducial assembly of claim 16, wherein said shaped body is selected from the group of shapes consisting of a circle, oval, triangle, square, rectangle, pentagon, hexagon, other polygon shape and an irregular shape.

20. The MRI compatible fiducial assembly of claim 17, wherein said shaped body has at least one lower body extending from said lower surface and wherein said bore extends through said lower body.

\* \* \* \* \*